United States Patent [19]
Wright et al.

[11] Patent Number: 5,405,969
[45] Date of Patent: Apr. 11, 1995

[54] MANUFACTURE OF THIOETHER COMPOUNDS

[75] Inventors: Charles W. Wright, Fairport; Joan C. Potenza, Rush; John E. Leary, Jr., Rochester; Chang K. Kim, Pittsford, all of N.Y.

[73] Assignee: Eastman Kodak Company, Rochester, N.Y.

[21] Appl. No.: 165,765

[22] Filed: Dec. 10, 1993

[51] Int. Cl.$^6$ ............... C07D 257/04; C07D 413/12; C07D 231/14; G03C 7/00

[52] U.S. Cl. .................. 548/250; 548/221; 548/225; 548/182; 548/144; 548/136; 548/251; 548/183; 548/183; 548/262.4; 548/366.7; 430/387; 430/505; 430/555; 430/372; 430/393; 430/558

[58] Field of Search ............ 548/250, 221, 225, 182, 548/144, 136, 251, 336, 363, 374, 376; 430/387, 505, 555, 372, 393, 558

[56] References Cited

U.S. PATENT DOCUMENTS

| | | | |
|---|---|---|---|
| 4,032,346 | 6/1977 | Furutachi et al. | 96/56.5 |
| 4,293,691 | 10/1981 | Furutachi et al. | 544/140 |
| 4,556,630 | 12/1985 | Furutachi et al. | 430/372 |
| 4,853,319 | 8/1989 | Krishnamurthy et al. | 430/387 |
| 4,855,441 | 8/1989 | Renner et al. | 548/363 |
| 4,918,085 | 4/1990 | D'Silva et al. | 548/376 |
| 5,104,994 | 4/1992 | Roberts et al. | 548/376 |

FOREIGN PATENT DOCUMENTS

3624103A 1/1988 Germany.
295364A5 10/1991 Germany.

OTHER PUBLICATIONS

Otto, H. H.; Preparation of 4–Artylthio–3–Methyl–1–Phenyl–2–Pyrazolin–5–Ones; Sep. 21, 1970; Arch. Pharmaz., 304/71, pp. 504–506. English Translation.

Rolf Runge et al.; CCl$_4$ As Mild Oxidant In Sulfur Chemistry III; Jul. 12, 1990; Sulfur Letters, vo., 12 (1+2), pp. 33–44. English Translation.

*Primary Examiner*—Arthur C. Prescott
*Attorney, Agent, or Firm*—Arthur E. Kluegel

[57] ABSTRACT

The invention provides a process for making a thioether compound having the formula:

$$A\text{—}S\text{—}R$$

comprising reacting:
(1) Compound I having the formula:

$$A\text{—}H \quad\quad (I)$$

where A comprises a carbon atom bonded to H where that carbon is either capable of ionizing to a nucleophilic state or is conjugated to such an atom, with
(2) Compound II having the formula:

$$H\text{—}SR \text{ or } RSSR \quad\quad (II)$$

wherein R is selected from the group consisting of:
(a) a substituted or-unsubstituted aryl group or alicyclic group, said groups being carbocyclic or heterocyclic, and
(b) a thiocarbonyl group,
in the presence of a base and an oxidizing agent that is free of reactive halogen and that is capable of oxidizing H—SR to RSSR.

34 Claims, No Drawings

MANUFACTURE OF THIOETHER COMPOUNDS

FIELD OF THE INVENTION

This invention relates to a method for the manufacture of thioether compounds by reacting a compound having a nucleophilic site with a thiol or disulfide in the presence of a base and an oxidizing agent.

BACKGROUND OF THE INVENTION

Thioether compounds are useful in many industries including those related to pharmaceuticals, agricultural chemicals, dyestuffs, and color photography. In color photography using silver halide-based light sensitive materials, a color image is obtained by the reaction of a color image forming coupler with the oxidation product of a color developing agent. The oxidized developer is formed upon development of exposed silver halide granules present in a gelatin emulsion layer which also contains the color image forming coupler. The two react to generate the dye of which the color image is formed. The color image forming materials (couplers) possess a site that is activated toward reaction with oxidized developer (the coupling site). It is common for couplers to possess a leaving group (coupling-off group) at the activated site. Couplers with such a structure allow for the theoretical use of only two moles of silver halide to generate one mole of dye and are thus called two equivalent couplers. Couplers without a coupling-off group are termed four equivalent couplers since theoretically four moles of silver must be used to obtain one mole of image-forming dye. In practice, the reactions are far less efficient, and much more than two or four equivalents is needed to achieve the desired degree of dye formation in either instance. The coupling-off group itself, which may be a photographically useful group (PUG), may serve a function such as carrying out color correction, assisting in the bleaching of unwanted silver, contributing to sharpness, or otherwise providing interimage effects. Another class of compounds that couple with oxidized developer to release photographically useful groups are those which form either colorless species or dyes that are not retained in the final image (U.S. Pat. No. 5,151,343) sometimes referred to as "universal" couplers. Thiol coupling off groups have been employed for all the above purposes and couplers which release them are valuable tools for obtaining desirable features in a photographic system. (U.S. Pat. Nos. 4,556,630 and 4,853,319)

A variety of methods exist for preparation of these thioether materials. The most widely used process is arylthiolation, and it consists of reacting a coupler which contains one or two hydrogens at the coupling site (a four equivalent coupler) with an activated derivative of the thiol which has been preformed in a separate step. The most common derivatives are sulfenyl halides 1, which are formed as described in U.S. Pat. No. 4,853,319 and U.S. Pat. No. 4,556,630 by reaction of either a thiol or a disulfide with a halogenating agent in a polar solvent such as dimethylformamide. Derivatives such as sulfenic acid amides 2, (U.S. Pat. No. 4,855,441), thiosulfonyl compounds 3, (DE 3,624,103), S(alkyl or arylthiol)isothioureas 4, (U.S. Pat. No. 4,293,691), thiuramdisulfides, thiocarbonyldisulfides and carbonyldisulfides 5, (U.S. Pat. No. 4,032,346) have also been described.

Thus, there have been employed the following thiolating reagents:

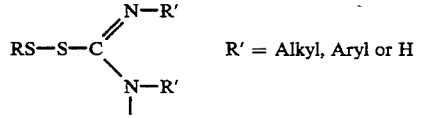

The sulfenyl halide method involves either formation of the sulfenyl halide in a separate step by addition of bromine, gaseous chlorine or a halogenating agent such as sulfuryl chloride to a disulfide or thiol in a polar solvent such as dimethylformamide followed by addition of the four equivalent coupler, or by introducing the halogenating agent into a mixture of the two reactants. There are numerous drawbacks to this method.

For example, the extent of sulfenyl halide formation cannot be ascertained with certainty. No good in-process assay is available for such a material, and it must be assumed that the reaction has gone to completion based on the amount of halogenating agent added. This can lead to yield and quality variations. Furthermore, halogenated impurities are generated by the side-reaction of the starting materials and products with free halide ions and radicals. These side-reaction products are undesirable and must be removed by a separate purification step. This results in lower yields and higher costs associated with an extra step and gives rise to the further problem of disposal of waste liquors.

As added disadvantages, it is noted that corrosive and difficult to handle reagents such as brominating reagents, are employed and that the process is not environmentally benign. High waste volumes are generated because of the need for extra purification and the halogenated wastes cannot be recycled in accordance with environmental regulations. They must be incinerated which increases costs and poses enough of an environmental threat to make production of large volumes of material via this route undesirable.

The other types of derivatives, 2–5, which have been described also must be prepared in a separate step. 2 and 3 are made through the intermediacy of the sulfenyl halide and therefore suffer from the aforementioned limitations regarding halogenation. Reagents 4 and 5 are both disadvantageous in their methods of preparation. The derivative 4 is prepared by oxidation of the thiol component in the presence of a thiourea with hydrogen peroxide. 5 is made by oxidation of the corresponding mercaptan with an appropriate oxidant as described in U.S. Pat. No. 4,032,346 and is not useful for introduction of simple alkyl or aryl thiol substituants. All these derivatives must be used in at least a 1:1 molar ratio with the four equivalent coupler and one half of the disulfide entity functions purely as a leaving group which does not react to form desired product. Half the reactant must therefore be separated from the final product and disposed of. Thus, the efficiency of this process is, at most, 50% based on the disulfide reactant.

Any strategy which employs one of these derivatives is costly due to the great number of steps involved, the lower throughput resulting from higher molecular weight intermediates, the amount of waste generated, and the molar stoichiometry required for complete product formation.

DD 295,364 appears to describe a reaction between diheterocyclic disulfides and active methylene compounds in acetic acid to provide heterocyclic thioethers. The reported yields are too low to be of commercial value. DE 3624 103 describes preparation of arylthiol pyrazalone couplers via reaction of the halogenated coupler parent with the anion of the desired thiol. U.S. Pat. No. 5,104,994 covers preparation of thiopyrazoles by two methods: 1) substitution of an amino substituent for a thio substituent by diazotization with butyl nitrite in the presence of a disulfide, and 2) reaction of the lithium salt of a pyrazole with a molar equivalent of a disulfide at low temperature. The lithiated pyrazole is pre-formed by halogen metal exchange of a bromo pyrazole with n-butyl lithium at low temperature. Practically, it would be very difficult to successfully carry out this reaction on a production scale basis.

Several other thiolation methods have been reported for active methylene compounds but they appear to be limited in scope and/or are not adaptable to large scale manufacture. The method of Otto et.al. (Arch. Pharmaz., 304, pp 504-506 (1971)), in which thiols are heated with pyrazalones in dimethylsulfoxide, has been reported to provide 4arylthio pyrazalones. The practicality of this method is limited to laboratory scale preparations because the excessively high reaction temperature (near 200° C.) would present a safety hazard in a large scale facility. The isolation of the products would require large wash volumes which would then have to be disposed of. When it was attempted to modify the conditions to those that would be safe and practical for commercial manufacture, it was found that the reaction did not proceed to completion at lower temperatures in the absence of a base. The method described was not extended to other couplers or other compounds containing active methylene or conjugated to such active compounds. Runge et.al. (Sulfur Letters, 12, (1+2), pp 33-44, (1990)) describes organothiolation of active methylene compounds in the presence of carbon tetrachloride and base. However, the presence of reactive halogen species in the mixture could lead to the same halogenated impurities produced by the sulfenyl halide method. These can produce undesirable effects if present in the final coupler. There are hazards associated with the use of a known carcinogen such as carbon tetrachloride and special precautions would have to be taken to use it commercially. Non-recoverable waste and disposal of halogenated liquors are deterents to the use of this method. In addition, no disclosure of it's application to photographically useful compounds is made.

In particular, what is needed is a process that uses reagents that are free from reactive halogen so that no unwanted halogenation of the reactants or products can take place to form undesirable halogenated impurities which contaminate the desired product, and so that there are no environmentally hazardous halogenated wastes which must be disposed of and no unsafe halogenated compounds to be handled.

In summary, there is a need for a more efficient, safer, and more environmentally favorable method for the manufacture of thioether-containing compounds.

SUMMARY OF THE INVENTION

The invention provides a process for making a thioether compound having the formula:

A—S—R comprising reacting:
(1) Compound I having the formula:

A—H  (I)

where A comprises a carbon atom bonded to H where that carbon is either capable of ionizing to a nucleophilic state or is conjugated to such an atom, with (2) Compound II having the formula:

H—SR or RSSR  (II)

wherein R is selected from the group consisting of:
(a) a substituted or unsubstituted aryl group or alicyclic group, said groups being carbocyclic or heterocyclic, and
(b) a thiocarbonyl group, in the presence of a base and an oxidizing agent that is free of reactive halogen and that is capable of oxidizing H—SR to RSSR.

The process provides improved efficiency without the difficulties associated with compounds containing reactive halogen.

DETAILED DESCRIPTION OF THE INVENTION

The mechanism for the process of the invention may be depicted by the following overall reaction scheme where the added reactant (Compound II) is the disulfide:

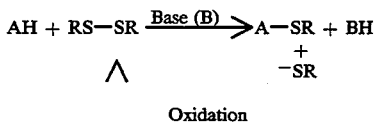

or if the thiol is the added reactant the reaction may be depicted as follows:

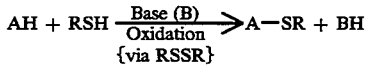

In the above reaction, A—H (Compound I) can be any compound containing a carbon atom bonded to a hydrogen atom which is either capable of ionizing to a nucleophilic state or is conjugated to such an atom. In the case where the compound is a photographic coupler, the compound will generally be one capable of coupling with the oxidation product of a photographic developer, which possesses at least one hydrogen atom at the active coupling site, or a compound which bears an active methylene group which is capable of ionizing to a nucleophillic state in the presence of a base. Suitable general formulas for compounds meeting the aforementioned requirements are shown in Table I. The site capable of reacting with Compound II is shown by an asterisk. (In some cases there is more than one possible site and the site may be influenced by the exact identity of the other substituents.)

Typically the group A will have up to 42 carbon atoms although higher numbers are possible.

TABLE I

6. R₁-C(=O)-CH*-C(=O)-NR₂(R₂)

7. R₃-C₆H₃(OH)(NHR₃)-*

8. Naphthalene with OH, CON(R₂)₂, R₃, *

9. Triazole with R₃, NH, R₃, *

10. Triazole with R₃, NH, R₃, *

11. R₄N-N=C(NR₄R₄)-CH*-C(=O)

12. Pyrazole with *, R₃, NH, R₃, R₃

13. NC-C*=C(NHR₄)-CN

14. Benzoxazole with R₃, *CH(R₅)(R₇)

TABLE I-continued

15. Benzene ring with W, W, =O, R₃, *; W = C,N

16. Indanone-type with R₃, Y, *, =O

17. Benzene fused ring with R₃, Y, *, =O; Y = N,O,S

18. Benzene with SO₂-NR₂-CH₂*, R₃

19. R₃-C₆H₄-C(=O)-CH*-C(tetrazole)

20. Acenaphthylenone with R₃, R₃, *, =O

21. *-C(R₆)=C(R₅)-N-C(=O)-O

22. Benzene with NR₄-SO₂-CH₂-C(=O)-*, R₃

23. Benzene with N=N-N=N thiadiazole fused, R₃, S, *

TABLE I-continued
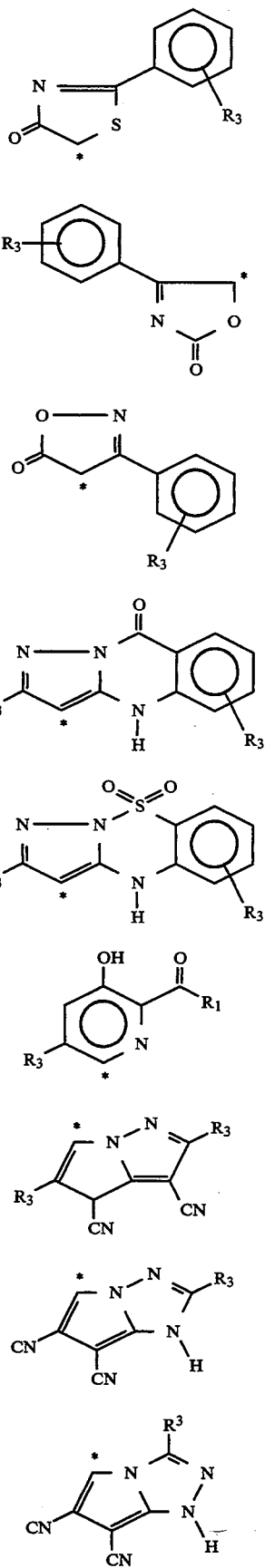
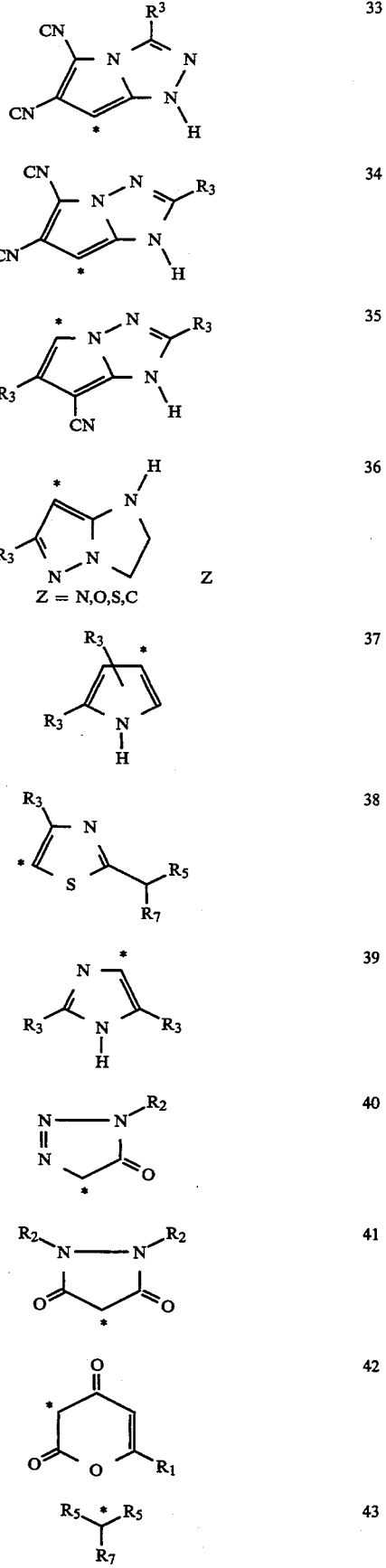

TABLE I-continued

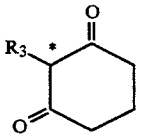 44

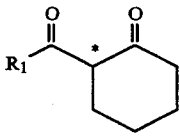 45

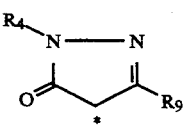 101

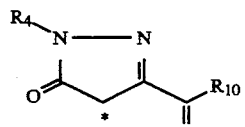 102

For Tables I and II:

R₁=hydrogen, hydroxy, or substituted or unsubstituted aryl, alkyl, heterocyclic, alkoxy, aryloxy, amino or hydrazino.

R₂=hydrogen, hydroxy, or substituted or unsubstituted aryl, alkyl, heterocyclic, alkoxy, aryloxy, amino, hydrazino, or acyl group.

R₃=hydrogen, hydroxy, halogen, nitro, cyano, carboxyl or substituted or unsubstituted aryl, alkyl, heterocyclic, alkoxy, aryloxy, amino or hydrazino, amido, sulfonamido, carbonyl, sulfamoyl, sulfone, sulfoxide, mercapto, ureido, carbamate, thiocarbonyl or carbonate group.

R₄=hydrogen, hydroxy, or substituted or unsubstituted aryl, alkyl, heterocyclic, alkoxy, aryloxy, amino or hydrazino, acyl, or sulfonyl group.

R₅=nitrile, nitro, halogen, or substituted or unsubstituted acyl, sulfone, sulfoxide, or sulfonamide group.

R₆=hydrogen, hydroxy, or substituted or unsubstituted aryl or alkyl.

R₇=hydrogen, halogen or substituted or unsubstituted aryl or alkyl group.

R₈=hydrogen, halogen or substituted or unsubstituted aryl, alkyl or acyl group.

R₉=hydrogen, or substituted or unsubstituted alkyl or aryl group.

R₁₀=substituted or unsubstituted alkyl, aryl, alkoxy, aryloxy, or amino.

X₂=substituted or unsubstituted alkoxy, aryloxy, amino or hydrazino group.

Ph=phenyl

Note: Two substituents may combine to form a ring.

As used herein, the term "substituted" or "substituent", unless otherwise specifically stated, has a broad definition. The substituent may be, for example, halogen, such as chlorine, bromine or fluorine; nitro; hydroxyl; cyano; and carboxy and its salts; and groups which may be further substituted, such as alkyl, including straight, branched chain and cyclic alkyl, such as methyl, trifluoromethyl, ethyl, t-butyl, 3-(2,4-di-t-amylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, a- or b-naphthyloxy, and 4-tolyloxy; carbonamido, such as acetamido, benzamido, butyramido, tetradecanamido, a-(2,4-di-t-pentyl-phenoxy)acetamido, a-(2,4-di-t-pentylphenoxy)butyramido, a-(3-pentadecylphenoxy)-hexanamido, a-(4-hydroxy-3-t-butylphenoxy)-tetradecanamido, 2-oxo-pyrrolidin-1-yl, 2-oxo-5-tetradecyl-pyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylcarbonylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-toluylcarbonylamino, N-methylureido, N,N-dimethylureido, N-methyl-N-dodecylureido, N-hexadecylureido, N, N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, and hexadecylsulfonamido; sulfamoyl, such as N-methylsulfamoyl, N,N-dipropylsulfamoylamino, N-ethylsulfamoyl, N,N-dipropylsulfamoyl, N-hexadecylsulfamoyl, N, N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; azo, such as phenylazo and naphthylazo; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

The particular substituents used may be selected to attain the desired photographic or other properties for a specific application and can include, for example, hydrophobic groups, solubilizing groups, blocking groups, etc. Generally, all of the "R" groups herein and substituents thereof may typically include those having 1 to 42 carbon atoms and often less than 30 carbon atoms, but greater numbers are possible depending on the particular substituents selected. Moreover, as indicated, the substituents may themselves be suitably substituted with any of the above groups.

Suitable Compound I's are those useful for coupling with an oxidized photographic color developer and containing a coupling group (COUP) and a coupling-off group (COG), comprising reacting Compound I with Compound II in the presence of a base, an oxidizing agent, and a solvent, wherein Compound I has a formula selected from the group consisting of:

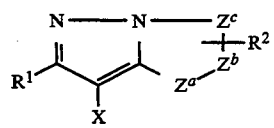
Compound I-1 and

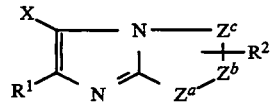
Compound I-2 and Compound II has the formula:

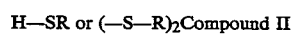
H—SR or (—S—R)$_2$ Compound II wherein $R^1$ and each $R^2$ are independently hydrogen or substituents that do not adversely affect the coupling action of the coupler; X is hydrogen; and $Z^a$, $Z^b$ and $Z^c$ are independently selected from the group consisting of a substituted or unsubstituted methine group, =N—, =C— or —NH—, provided that one of either the $Z^a$-$Z^b$ bond or the $Z^b$-$Z^c$ bond is a double bond and the other is a single bond, and when the $Z^b$-$Z^c$ bond is a carbon-carbon double bond, it may form part of an aromatic ring, and wherein at least one of $Z^a$, $Z^b$ and $Z^c$ represents a methine group connected with the group $R^2$; and R is (1) an aryl or alicyclic group, said group being carbocyclic or heterocyclic, or (2) a thiocarbonyl group.

More particular examples for Compound I have a formula such as:

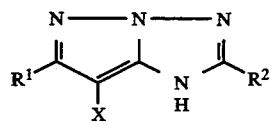
I-3

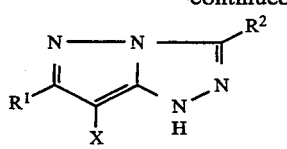
I-4

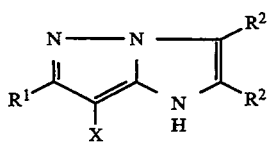
I-5

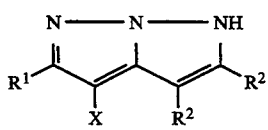
I-6

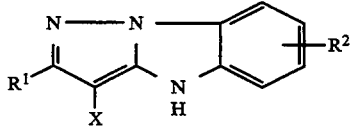
I-7

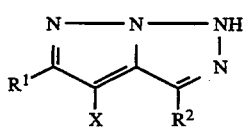
I-8

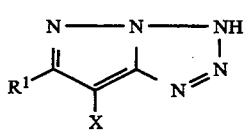
I-9

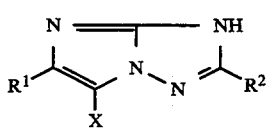
I-10

Other suitable Compound I's may be selected from I-11 through I-16:

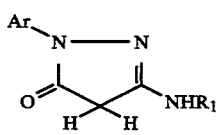
I-11 wherein:

Ar is an unsubstituted aryl group or an aryl group substituted with one or more substituents selected from halogen atoms and cyano, alkylsulfonyl, arylsulfonyl, sulfamoyl, sulfonamido, carbamoyl, carbonamido, alkoxy, acyloxy, aryloxy, alkoxycarbonyl, aryloxycarbonyl, ureido, nitro, alkyl, and trifluoromethyl, or Ar is an aryl group substituted with a group which forms a link to a polymeric chain;

$R_1$ is a substituted or unsubstituted acyl or phenyl group, the substituents of $R_1$ being individually selected from halogen atoms, and alkyl, aryl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyl, acyloxy, ureido, imido, carbamate, heterocyclic, cyano, trifluoromethyl, alkylthio, nitro, carboxyl and hydroxyl groups, provided that $R_1$ contains at least 6 carbon atoms or the $R_1$ substituents may individually comprise a group which forms a link to a polymeric chain;

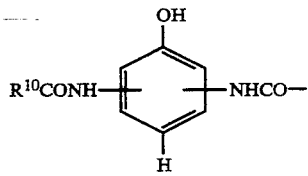   I-12

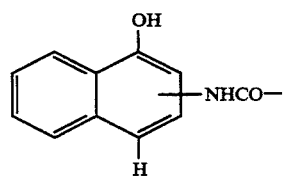   I-13 and

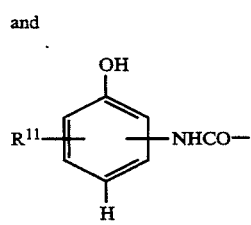   I-14 wherein $R^{10}$ represents a ballast group or a substituted or unsubstituted alkyl or aryl group; and $R^{11}$ represents one or more halogen atoms, alkyl having 1 to 4 carbon atoms or alkoxy having 1 to 4 carbon atoms; and

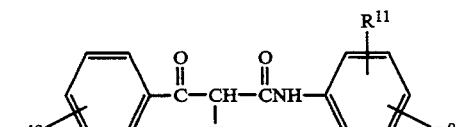   I-15 and

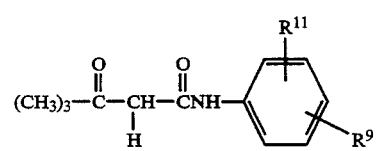   I-16 where $R^{10}$ represents a ballast group or a substituted or unsubstituted alkyl or aryl group, $R^9$ is selected from the group consisting of hydrogen, a ballast group, or unsubstituted or substituted alkoxy, alkoxycarbonyl, alkanesulfonyl, arenesulfonyl, aryloxycarbonyl, carbonamido, carbamoyl, sulfonamido, or sulfamoyl, $R^{11}$ is hydrogen or one or more halogen, lower alkyl, lower alkoxy, or a ballast group.

Compound II may be a disulfide or thiol bonded to (1) a substituted or unsubstituted aryl group or alicyclic group, said groups being carbocyclic or heterocyclic, or (2) a thiocarbonyl group. In the event that the corresponding thiol is more readily accessible, it can be used and then disulfide is formed in-situ by the action of the oxidant as shown in the proposed reaction scheme. Normally the group R has 42 carbon atoms or less but more are possible. Typical examples of thiol/disulfide compounds which can be used in the present invention are shown in Table II.

TABLE II (Structures 46–55 shown)

TABLE II-continued

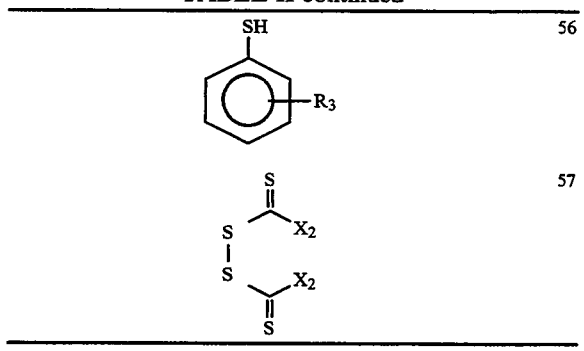

For Table II substituents see Table I footnotes.

Thiocarbonyl substituents can serve as precursors to other mercapto moieties via hydrolysis and subsequent functionalization as shown in the following scheme:

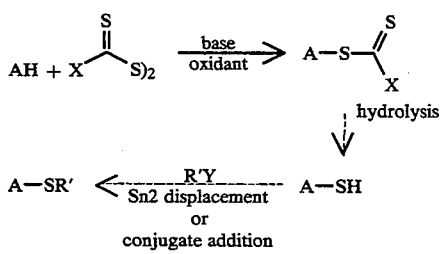

$X = X_2$ as described in the footnote to Table I including for example $NH_2$, $NHR$, $NR_2$;

Y = a leaving group such as halogen or sulfonyloxy including, for example, $-OSO_2CH_3$, $-OSO_2CF_3$, or $-OSO_2$—phenyl.

R' = substituted or unsubstituted alkyl.

For example, compounds such as the ones shown below may be synthesized by this technology:

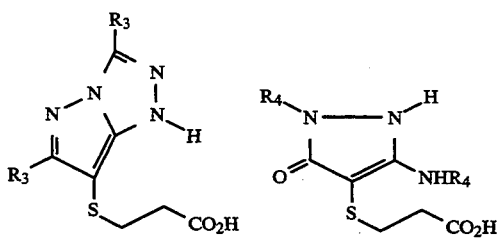

A suitable molar ratio of disulfide to active methylene component is 0.5:1 to 1:1, the most efficient range being 0.5:1 to 0.7:1. Lower ratios may provide a greater degree of efficiency but higher ratios may provide more desirable kinetics.

While not essential in every instance, it is generally desirable to have present during the reaction a solvent for the reactants. Suitable solvents are those that dissolve the components of the reaction but do not react with them. The choice of solvent is best made on an individual basis for each combination of reactants and may be chosen in order to maximize rate, yield, cost, and product quality. Suitable solvents include alcohols (e.g. methanol, isopropanol or ethanol), esters (e.g. ethyl or propyl acetate), ketones (e.g. acetone, methyl ethyl ketone), polar aprotics (e.g. dimethylformamide, N-methyl pyrrolidone, dimethyl sulfoxide), ethers (e.g. tetrahydrofuran, dioxane, isopropyl ether), hydrocarbons (e.g. toluene, xylenes, heptane), halocarbons (e.g. methylene chloride), nitriles (e.g. acetonitrile, butyronitrile), water and mixtures of any of the above. The preferred choices are esters, alcohols, nitriles, ethers and polar aprotics.

Of course a single reaction component may function in a dual capacity. For example, a component may function both as both an oxidizing agent and a solvent as is the case with compounds containing a sulfoxide or an amine-N-oxide.

The reaction may be run at $-10°$ C. to $200°$ C., preferably between $20°$ C. $-100°$ C. The optimum temperature range is dependent on the specific components selected and their rate of reaction. A suitable concentration, based on the active methylene component, is 0.05M to 0.5M, with 0.1M to 0.3M being preferred.

Large amounts of base are not usually required to achieve the desired yield and kinetics. The amount required and the nature of the base depend on the acidity of both the active methylene and thiol components and are best determined individually for each combination of reactants. Typical molar ratios of base to active methylene component are 0.5:1 to 5:1. Most reactions give a successful outcome with a 1:1 to 2:1 ratio. Both organic and inorganic bases may be used. The conjugate acid of the base used may have a pKa in the range of 4 to 20 as defined by Gordon and Ford in *The Chemist's Companion*, Wiley and sons, Inc. N.Y., 1972, p.54-64. Typical examples of bases that may be used are ammonium and alkali metal salts of organic acids (eg. sodium or potassium acetate), carbonates, alkoxides and hydroxides, potassium fluoride, aromatic and aliphatic amines, guanidines, and amidines.

The oxidizing agent may be a chemical compound or it may be an electrochemical cell. Where a compound is employed as the oxidizing agent, the oxidant is present in at least a 0.5:1 molar ratio to the disulfide used or a 1:1 ratio with the thiol. Typically a 2 to 5 molar excess of oxidant may be employed. The oxidant must be strong enough to oxidize the corresponding thiol to the disulfide but not strong enough to promote further unwanted oxidation. The oxidant must function by a means other than halogenation of any of the components of the reaction. The oxidant may contain halogen that is not capable of generating free halogen, halide radicals or halide ions which can, under the reaction conditions, participate in the reaction. Typical examples of such oxidants are sulfoxides, amine-N-oxides, supplemented molecular oxygen (with or without a catalyst), metal oxides or other metal compounds (e.g. lead tetraacetate), azodicarboxylate/phosphine combinations, nitroso compounds, sulfoxonium salts, hypervalent iodine compounds, hydroperoxides. If desired, it is also within the scope to effect the desired oxidation via electrochemical methods. Preferred reagents for use in the present invention are sulfoxides, amine-N-oxides and supplemented molecular oxygen, with or without a catalyst.

In the case of molecular oxygen, it is not possible to simply rely on ambient oxygen to produce the desired thiol compounds in commercial quantities. The process must employ a means of supplementing the available oxygen beyond that available directly from the atmosphere in order to achieve a practical rate of reaction. Mechanical addition and/or catalytic assistance can provide the desired results.

When electrochemical means are employed, any conventional means that supplies the desired ability to convert the thiol to the disulfide will suffice.

The reaction may be followed by thin layer chromatography and is generally complete in 0.5 to 24 hours. A typical reaction time is 2 to 5 hours. The desired product can be isolated by extraction or crystallization after acidification to pH 6.5 or less. The excess oxidant and its by-products may be removed by washing with water and/or dilute acid. Typical examples of the synthesis of couplers by the present invention are illustrated below.

SYNTHESIS EXAMPLE 1

Preparation of compound 65.

To a stirred solution of 6-methyl-3[-3-4-nitrophenyl-propyl]-1H-pyrazolo(5,1-c)-1,2,4-triazole (1.49 g, 0.005 mol) in 20 ml of 1:1 dimethylformamide : ethyl acetate was added triethylamine (1.01 g, 0.01 mol), and phenyl mercaptotetrazole 46, $R_4$=phenyl (0.89 g, 0.005 mol). After stirring for 5 min, N-methylmorpholine-N-oxide was added as a 60% wt/wt solution in water (2.92 g, 0.015 mol). The mixture was heated to reflux and stirred for 20 hours. It was then diluted with ethyl acetate and washed successively with 0% aq. HCl saturated brine, water, and saturated brine. The organic phase was dried over $MgSO_4$, filtered and concentrated to provide a yellow solid. Recrystallization from ethyl acetate / cyclohexane provided 1.84 g of tan powder (79.8%), mp=184°-186° C., M/e =461. The product exhibited spectral properties that were consistent with the reported structure.

SYNTHESIS EXAMPLE 2

Preparation of compound

To a stirred solution of 1-hydroxy-n-(2-dodecyloxy-5-methyl)phenyl-2-naphthylamide (1.54 g, 0.0034 mol) in dimethylformamide (25 mL) was added disulfide 55, $R_1$=$CH_3$, $R_2$=$R_3$=H, (0.55 g, 0.0017 mol) followed by potassium acetate (0.33 g, 0.0034 mol) and N-methyl morpholine-N-oxide as a 60% wt/wt solution in water (2.65 g, 0.0136 mol). The mixture was heated to 70-75° C. and stirred for 20 hours. The cooled reaction mixture was poured into water and the precipitated solid was collected by filtration, then slurried in 10% aqueous HCl refiltered and washed with water. The solid was air dried to provide 1.76 g (82.6%) of a tan solid, mp=146°-148° C., M/e =627, which exhibited spectral properties consistent with the reported structure.

SYNTHESIS EXAMPLE 3

Preparation of compound 61.

To a stirred solution of N,N(dithiodi-2,1-phenylene)-bis(2-(2,4(1,1-dimethylpropyl)phenoxy) butanamide (137 g, 0.167 mol) in ethyl acetate (1645 mL) was added N-methylmorpholine-N-oxide (96 g, 0.482 mol) as a 60% wt/wt solution in water, followed by N-(4-chloro-3-(4,5-dihydro-5-oxy-1-(2,4,6-trichlorophenyl)pyrazo 1-3-ylamino)phenyl)tetradecamide (185 g, 0.300 mol) and potassium acetate (31.5 g, 0.321 mol). The mixture was heated to 70° C. and stirred for 4 hours. To it was then added about 1 L of a mixture of brine : dilute HCl. After shaking and separation, the organic phase was washed with additional portions of brine while still warm, dried with $MgSO_4$ and filtered. The filtrate was seeded, then diluted with acetonitrile and cooled. The resulting solid was collected, washed with ethyl acetate and air dried to provide 279 g (89.4%) of a fine tan solid. Mp=202° C., M/e=1040. Spectral properties were consistent with the reported structure.

Additional examples of compounds that can be prepared by this method are shown in Table III.

TABLE III

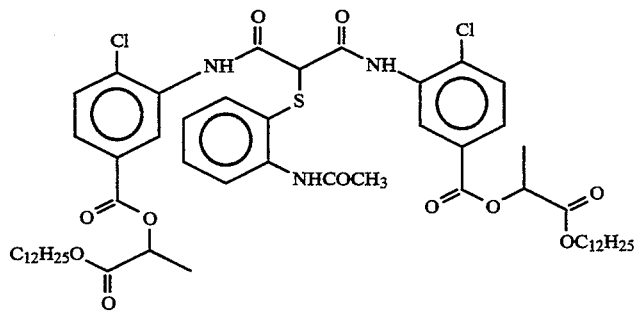

58

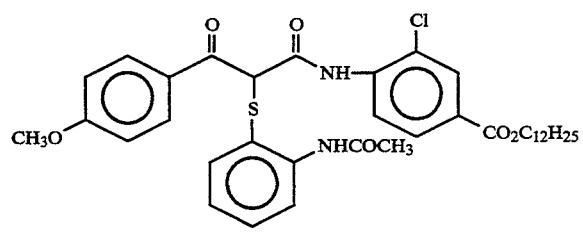

59

TABLE III-continued
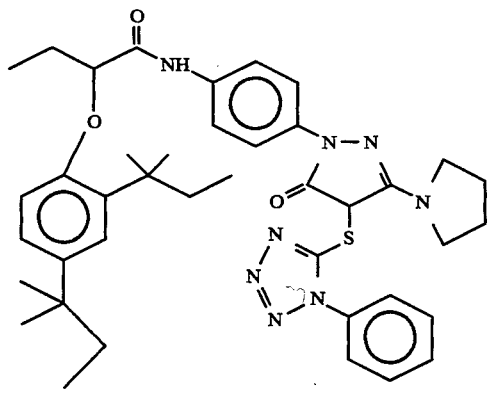
60
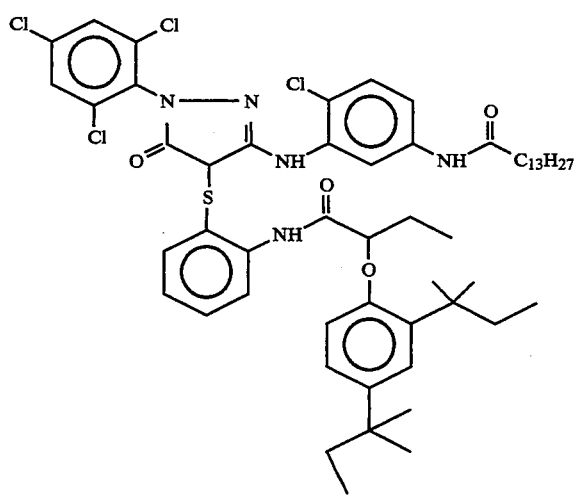
61
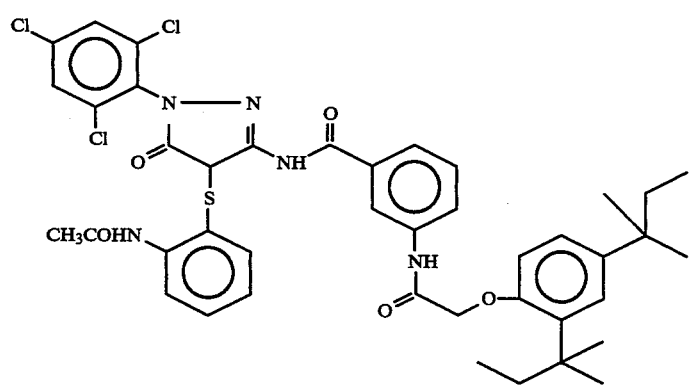
62
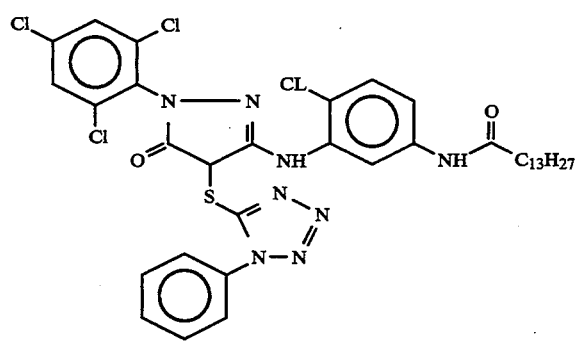
63

TABLE III-continued
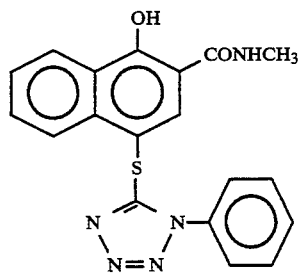
64
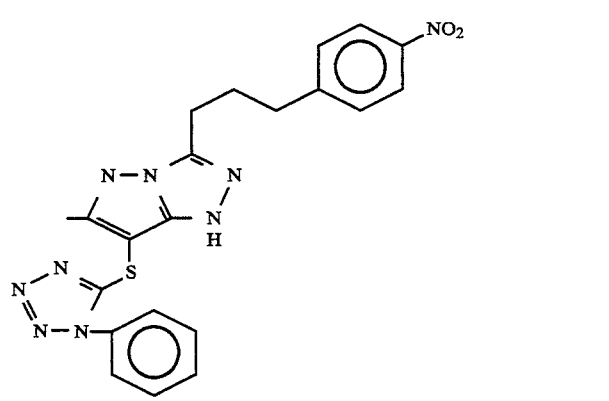
65
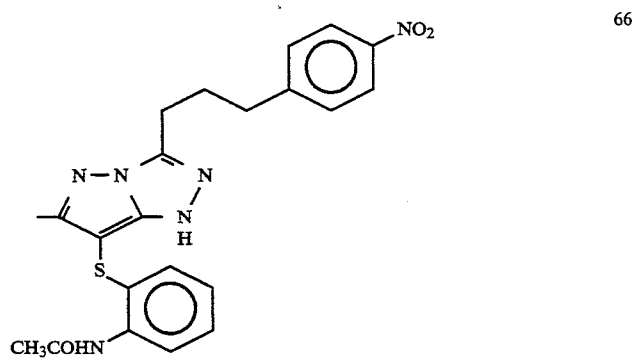
66
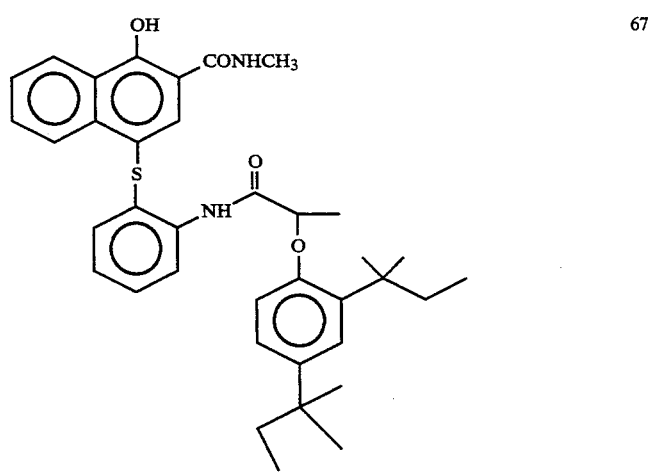
67

TABLE III-continued
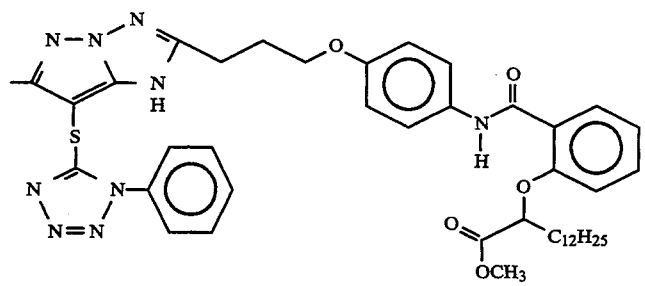
68
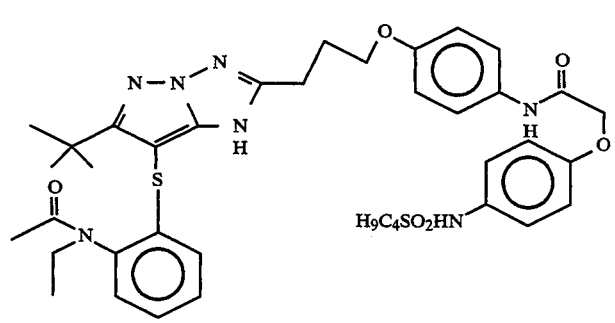
69
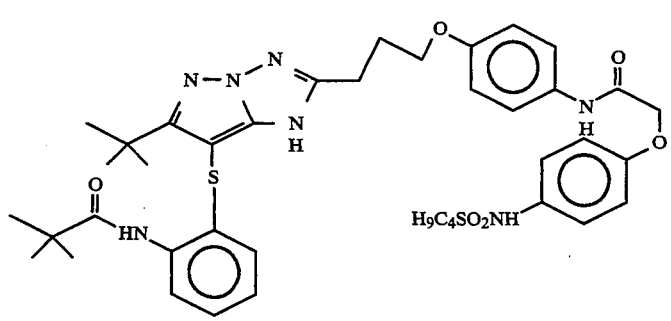
70
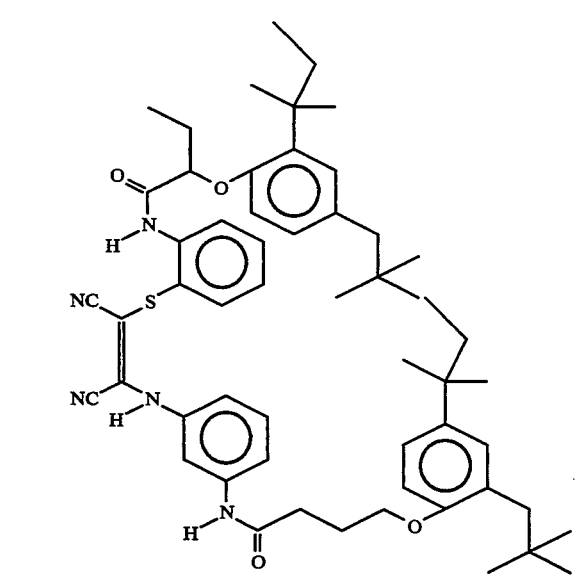
71

TABLE III-continued
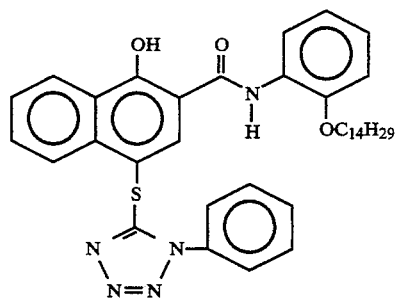
72
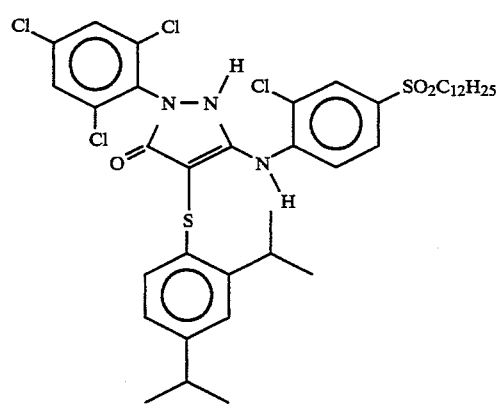
73
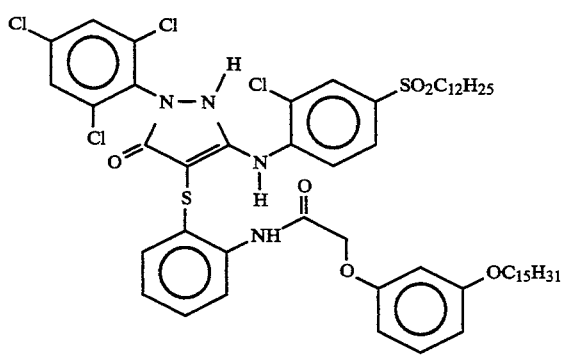
74
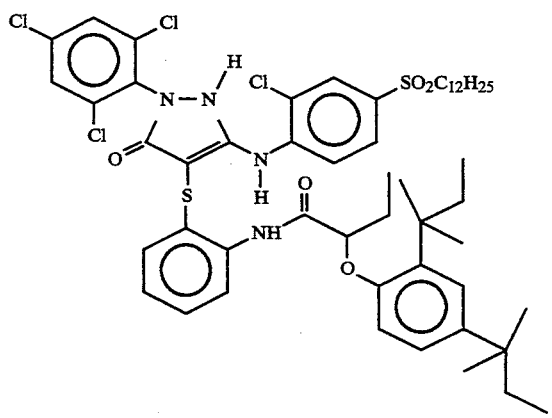
75

TABLE III-continued
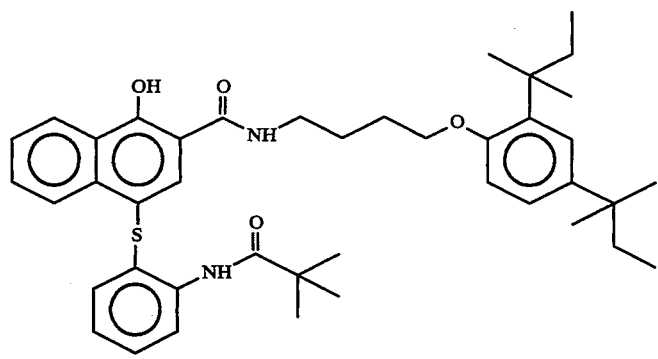
76
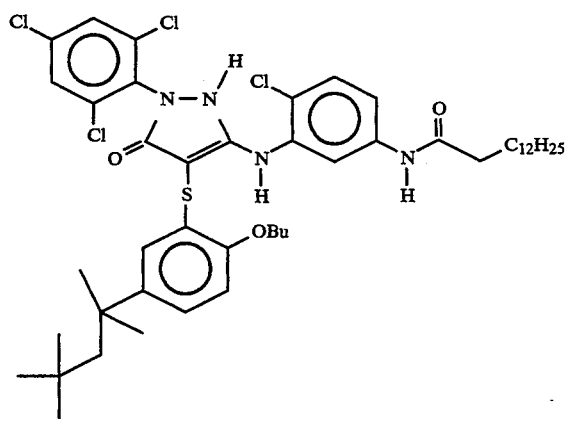
77
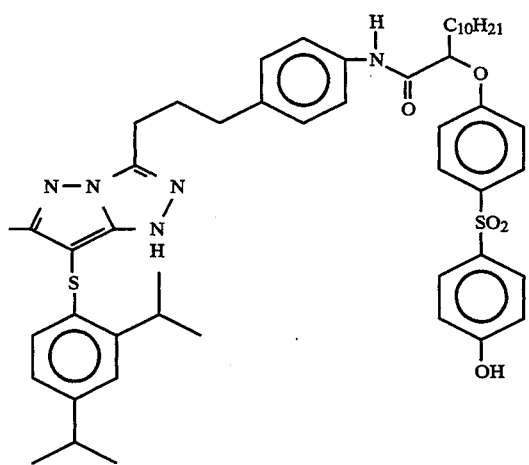
78
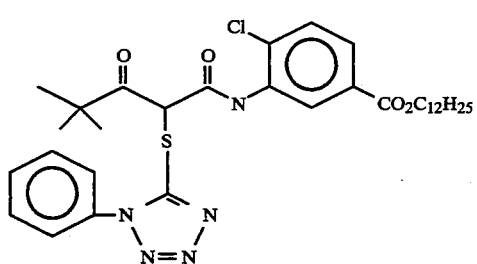
79

TABLE III-continued
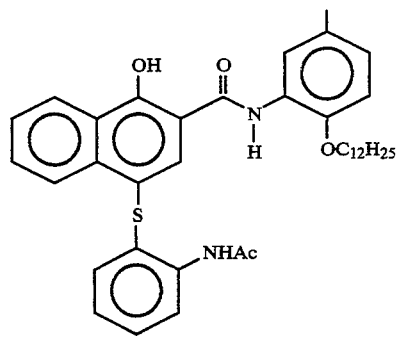
80
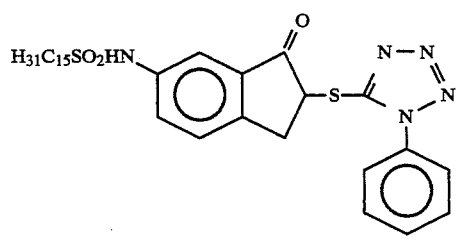
81
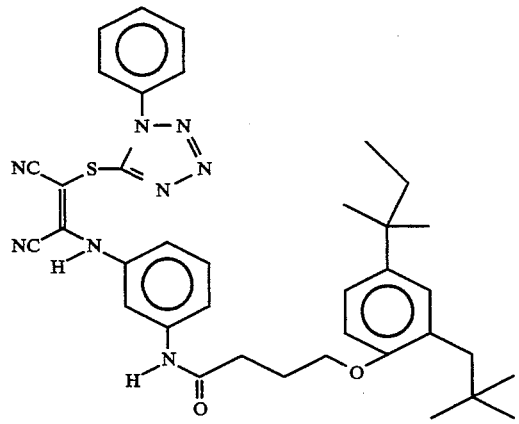
82
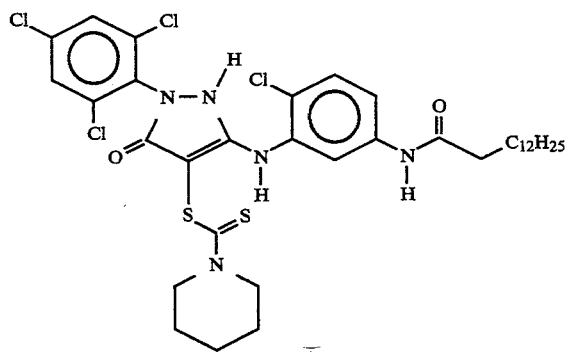
83

TABLE III-continued
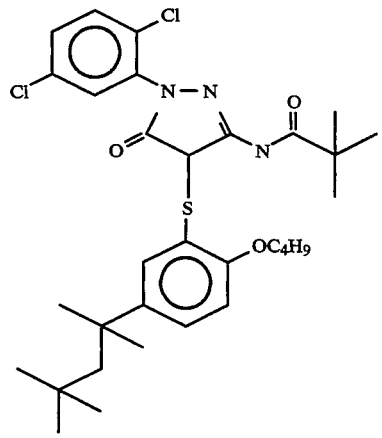
84
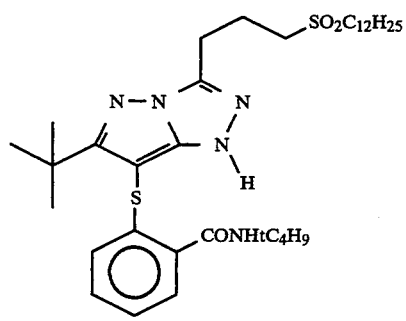
85
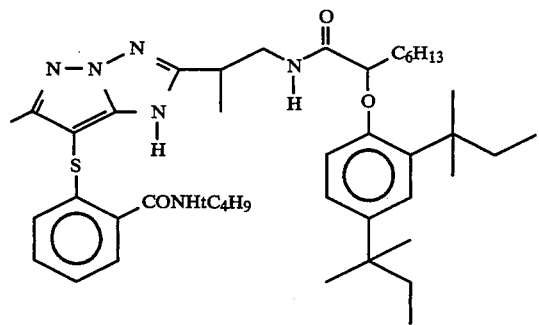
86
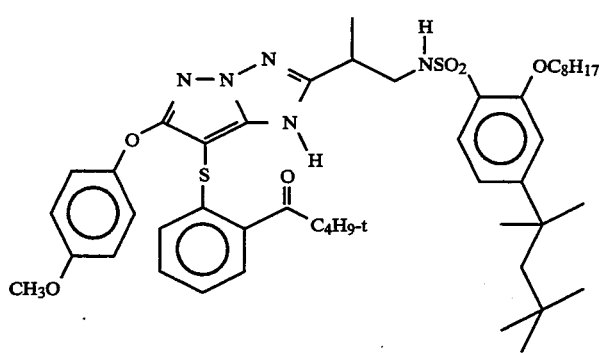
87

TABLE III-continued
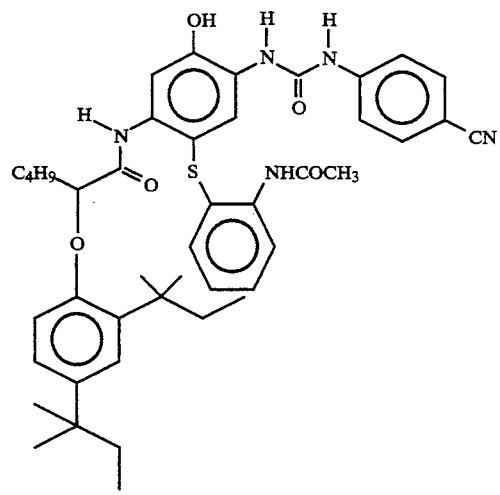
88
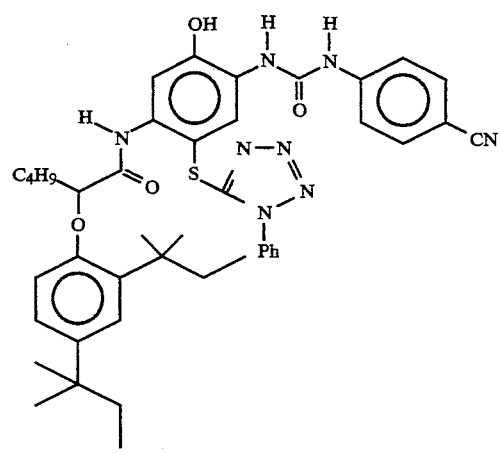
89
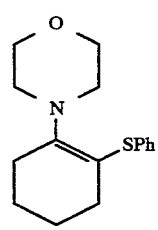
90
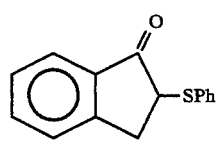
91
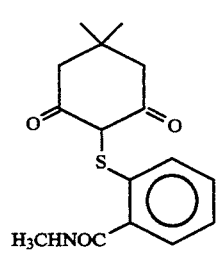
92

TABLE III-continued

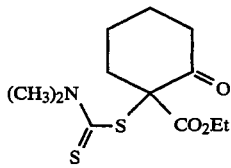 93

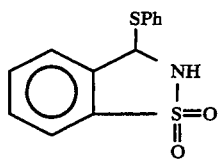 94

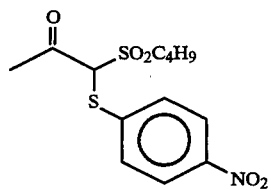 95

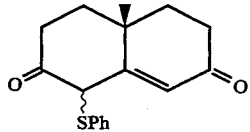 96

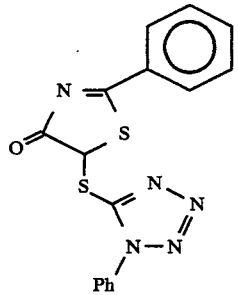 97

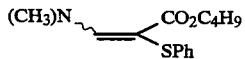 98

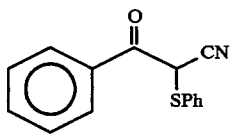 99

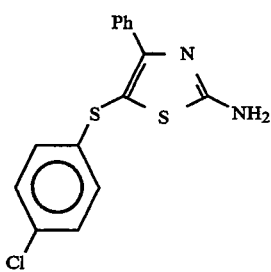 100

The object of the invention is to provide a more efficient, more cost effective and more environmentally favorable method for the manufacture of thioether-containing photographic couplers. The invention offers advantages over existing methods in the following areas:

The process uses reagents that are free from reactive halogen (eg. molecular halogen, halide ions or radicals). No unwanted halogenation of the reactants or products can take place. Undesirable halogenated impurities do not contaminate the product. Environmentally hazardous halogenated wastes which must be disposed of are not generated.

It is highly efficient in terms of stoichiometry. Essentially all parts of the disulfide reactant are converted to product. As displacement occurs on the disulfide to release an equivalent of thiol, the thiol is oxidized immediately back to disulfide which can participate in the reaction rather than creating a disposal problem. Less than one molar equivalent of disulfide is required for completion of the reaction The disulfide component, or its corresponding thiol, can be used as is, without conversion to an activated derivative. This streamlines the process, eliminates extra steps and uncertainty surrounding the extent of formation of the activated derivative, if it is made in-situ.

Throughput is excellent. No large quenching volumes are required and fewer purification steps are needed. Waste volumes are small relative to other processes and easy to recover solvents can be employed.

No highly toxic, difficult to dispense, environmentally hazardous or costly reagents need be employed. Moderate temperature ranges are used. Operator safety is maximized. The reaction conditions are mild and easily tolerated by a wide variety of functional groups.

The process is general in that it can be applied to any compound having an active methylene group including photographic couplers.

The present invention has been described in detail with particular reference to preferred embodiments, but it will be understood that variations and modifications can be effected within the spirit and the scope of the invention.

What is claimed is:

1. A process for making a thioether compound having the formula:

A—S—R comprising reacting:
(1) Compound I having the formula:

A—H     (I)

where A comprises a carbon atom bonded to H where that carbon is either capable of ionizing to a nucleophilic state or is conjugated to such an atom, with (2) Compound II having the formula:

H—SR or RSSR     (II)

wherein R is selected from the group consisting of:
(a) a substituted or unsubstituted aryl group or alicyclic group, said groups being carbocyclic or heterocyclic, and
(b) a thiocarbonyl group,
in the presence of a base and an oxidizing agent that is free of reactive halogen and that is capable of oxidizing H—SR to RSSR.

2. The process of claim 1 wherein Compound A—H is selected from the group consisting of the compounds depicted in Table I:

TABLE I

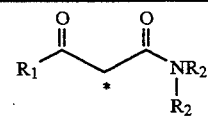  6

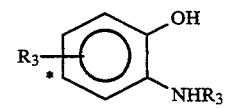  7

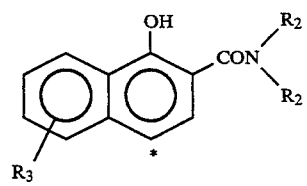  8

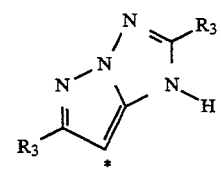  9

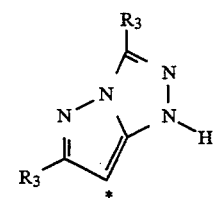  10

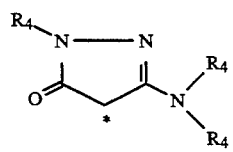  11

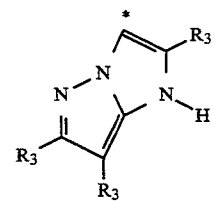  12

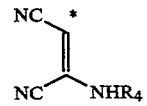  13

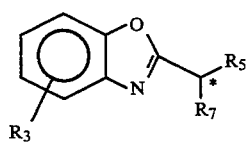  14

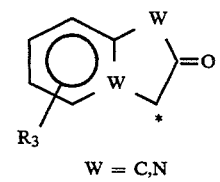  15

W = C,N

TABLE I-continued

TABLE I-continued

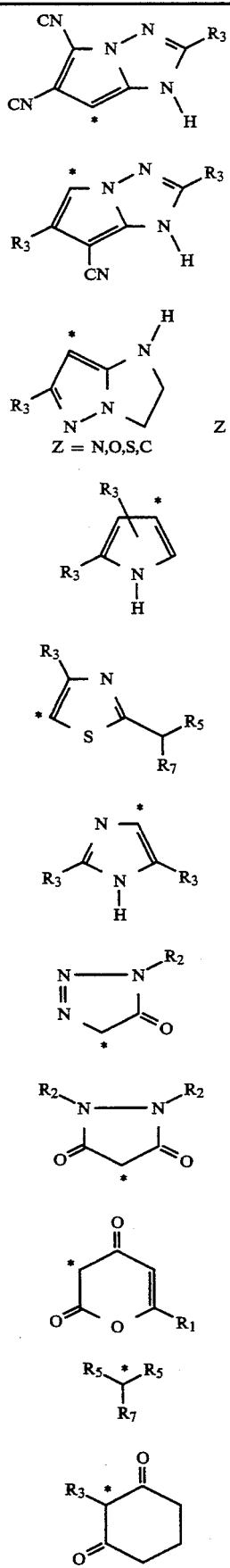
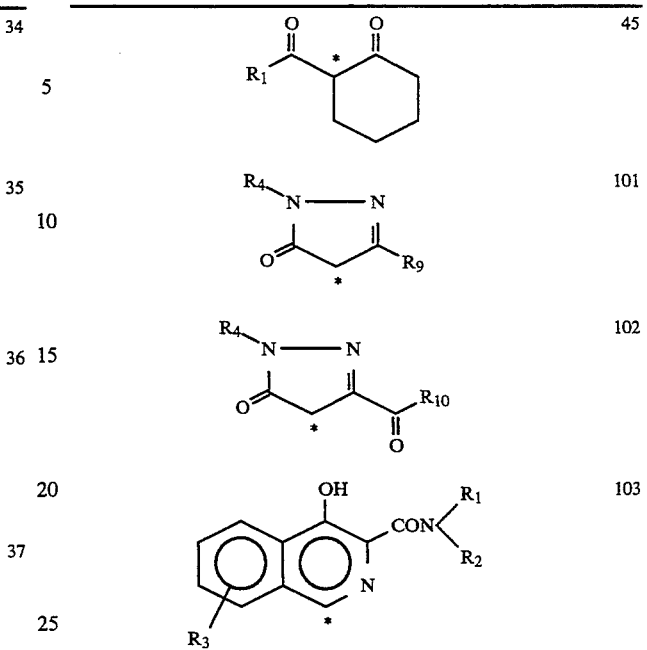

where:
- $R_1$ = hydrogen, hydroxy, or substituted or unsubstituted aryl, alkyl, heterocyclic, alkoxy, aryloxy, amino or hydrazino;
- $R_2$ = hydrogen, hydroxy, or substituted or unsubstituted aryl, alkyl, heterocyclic, alkoxy, aryloxy, amino, hydrazino, or acyl group;
- $R_3$ = hydrogen, hydroxy, halogen, nitro, cyano, carboxyl or substituted or unsubstituted aryl, alkyl, heterocyclic, alkoxy, aryloxy, amino or hydrazino, amido, sulfonamido, carbonyl, sulfamoyl, sulfone, sulfoxide, mercapto, ureido, carbamate, thiocarbonyl or carbonate group;
- $R_4$ = hydrogen, hydroxy, or substituted or unsubstituted aryl, alkyl, heterocyclic, alkoxy, aryloxy, amino or hydrazino, acyl, or sulfonyl group;
- $R_5$ = nitrile, nitro, halogen, or substituted or unsubstituted acyl, sulfone, sulfoxide, or sulfonamide group.
- $R_6$ = hydrogen, hydroxy, or substituted or unsubstituted aryl or alkyl;
- $R_7$ = hydrogen, halogen or substituted or unsubstituted aryl or alkyl group;
- $R_8$ = hydrogen, halogen or substituted or unsubstituted aryl, alkyl or acyl group;
- $R_9$ = hydrogen, or substituted or unsubstituted alkyl or aryl group;
- $R_{10}$ = substituted or unsubstituted alkyl, aryl, alkoxy, aryloxy, or amino;
- $X_2$ = substituted or unsubstituted alkoxy, aryloxy, amino or hydrazino group;
- Ph = phenyl where in those foregoing compounds containing two or more substituents, two substituents may combine to form a ring.

3. The process of claim 1 wherein Compound A—H is a compound selected from the group consisting of the pyrazolones, bicyclic azoles, diketomethylenes, phenols, naphthols and enamines, all substituted or unsubstituted.

4. The process of claim 1 wherein Compound II is selected from the group consisting of either a disulfide or a thiol bonded to a substituted or unsubstituted aryl group or alicyclic group, said groups being carbocyclic or heterocyclic.

5. The process of claim 1 wherein Compound II is selected from the group consisting of those depicted in Table II:

TABLE II

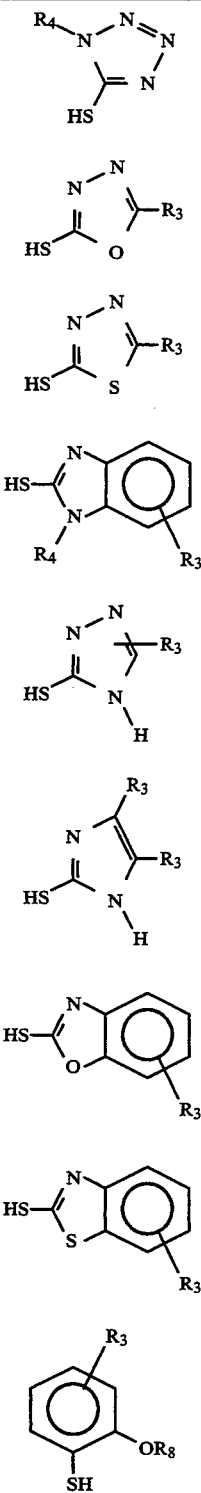

TABLE II-continued

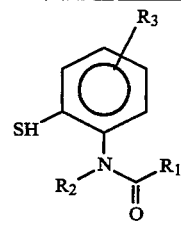

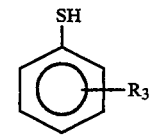

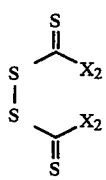

where:

R$_1$=hydrogen, hydroxy, or substituted or unsubstituted aryl, alkyl, heterocyclic, alkoxy, aryloxy, amino or hydrazino;

R$_2$=hydrogen, hydroxy, or substituted or unsubstituted aryl, alkyl, heterocyclic, alkoxy, aryloxy, amino, hydrazino, or acyl group;

R$_3$=hydrogen, hydroxy, halogen, nitro, cyano, carboxyl or substituted or unsubstituted aryl, alkyl, heterocyclic, alkoxy, aryloxy, amino or hydrazino, amido, sulfonamido, carbonyl, sulfamoyl, sulfone, sulfoxide, mercapto, ureido, carbamate, thiocarbonyl or carbonate group;

R$_4$=hydrogen, hydroxy, or substituted or unsubstituted aryl, alkyl, heterocyclic, alkoxy, aryloxy, amino or hydrazino, acyl, or sulfonyl group;

R$_5$=nitrile, nitro, halogen, or substituted or unsubstituted acyl, sulfone, sulfoxide, or sulfonamide group;

R$_6$=hydrogen, hydroxy, or substituted or unsubstituted aryl or alkyl;

R$_7$=hydrogen, halogen or substituted or unsubstituted aryl or alkyl group;

R$_8$=hydrogen, halogen or substituted or unsubstituted aryl, alkyl or acyl group;

R$_9$=hydrogen, or substituted or unsubstituted alkyl or aryl group;

R$_{10}$=substituted or unsubstituted alkyl, aryl, alkoxy, aryloxy, or amino;

X$_2$=substituted or unsubstituted alkoxy, aryloxy, amino or hydrazino group;

Ph=phenyl where in those foregoing compounds containing two or more substituents, two substituents may combine to form a ring.

6. The process of claim 1 wherein the oxidizing agent is an electrochemical cell of sufficient strength to oxidize the thiol corresponding to Compound II to the disulfide but not sufficient to oxidize the disulfide further.

7. The process of claim 1 wherein the oxidizing agent is a compound of sufficient strength to oxidize the thiol corresponding to Compound II to the disulfide but not sufficient to oxidize the disulfide further.

8. The process of claim 7 wherein the oxidizing agent is selected from the group consisting of supplemented molecular oxygen, sulfoxides, amine-N-oxides, azodicarboxylate/phosphine combinations, nitroso compounds, sulfoxonium salts, hypervalent iodine compounds, and hydroperoxides.

9. The process of claim 7 wherein the oxidizing agent is selected from the group consisting of supplemented molecular oxygen, a sulfoxide, and an amine-N-oxide.

10. The process of claim 7 wherein the oxidizing agent is selected from the group consisting of supplemented molecular oxygen, dimethyl sulfoxide, and N-methylmorpholine-N-oxide.

11. The process of claim 1 wherein the reaction occurs in the presence of a catalyst.

12. The process of claim 1 wherein the base is one having a $pK_a$ in the range of 4 to 20.

13. The process of claim 12 wherein the base is selected from the group consisting of the ammonium and alkali metal salts of organic acids, carbonates, alkoxides, and hydroxides; potassium fluoride; aromatic and aliphatic amines; guanidines; and amidines.

14. The process of claim 13 wherein the base is selected from the group consisting of the ammonium and alkali metal salts of acetic acid, triethylamine, and tetramethylguanidine.

15. The process of claim 1 wherein there is present during the reaction a solvent compound capable of dissolving Compound I and Compound II.

16. The process of claim 15 wherein the solvent is selected from the group consisting of water and alcohol, ester, ketone, polar aprotic, ether, hydrocarbon, nitrile, halocarbon, and sulfoxide compounds.

17. The process of claim 16 wherein the solvent is selected from the group consisting of methanol, isopropanol, ethanol, ethyl acetate, propyl acetate, acetone, methyl ethyl ketone, dimethylformamide, N-methyl pyrrolidone, dimethyl sulfoxide, tetrahydrofuran, dioxane, isopropyl ether, toluene, xylene, heptane, methylene chloride, acetonitrile, butyronitrile, water, and mixtures of the foregoing.

18. The process of claim 15 wherein one compound functions as both the solvent and the oxidizing agent.

19. The process of claim 1 wherein at least some of Compound II is formed in situ by the addition of the thiol of Compound II to the reaction whereby the thiol is oxidized to the disulfide.

20. A process for making a compound capable of coupling with an oxidized photographic color developer and containing a coupling group (COUP) and a coupling-off group (COG), comprising reacting Compound I, which is a compound capable of coupling with an oxidized color developer and having a group that is either capable of ionizing to a nucleophilic state or that is conjugated to such a group, with Compound II, which is a disulfide or thiol of a group corresponding to the desired COG or a precursor of either, in the presence of a base, an oxidizing agent free of reactive halogen, and a solvent.

21. A process for making a compound capable of coupling with an oxidized photographic color developer and containing a coupling group (COUP) and a coupling-off group (COG), comprising reacting Compound I, which is a 1-aryl-2-pyrazolin-5-one compound having a formula corresponding to the desired COUP and having two hydrogen atoms on the carbon at the 4-position, with Compound II, which is a disulfide or thiol of a group corresponding to the desired COG or a precursor of either, in the presence of a base, an oxidizing agent free of reactive halogen, and a solvent.

22. A process for making a compound capable of coupling with an oxidized photographic color developer and containing a coupling group (COUP) and a coupling-off group (COG), comprising reacting Compound I with Compound II in the presence of a base, an oxidizing agent, and a solvent, wherein Compound I has a formula selected from the group consisting of:

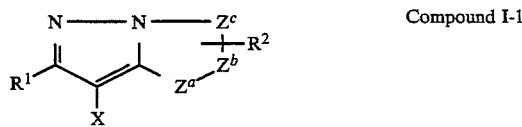

Compound I-1 and

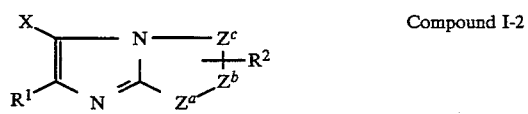

Compound I-2 and Compound II has the formula:

Compound II wherein $R^1$ and each $R^2$ are independently hydrogen or substituents that do not adversely affect the coupling action of the coupler; X is hydrogen; and $Z^a$, $Z^b$ and $Z^c$ are independently selected from the group consisting of a substituted or unsubstituted methine group, $=N-$, $=C-$ or $-NH-$, provided that one of either the $Z^a$-$Z^b$ bond or the $Z^b$-$Z^c$ bond is a double bond and the other is a single bond, and when the $Z^b$-$Z^c$ bond is a carbon-carbon double bond, it may form part of an aromatic ring, and wherein at least one of $Z^a$, $Z^b$ and $Z^c$ represents a methine group connected with the group $R^2$; and R is (1) an aryl or alicyclic group, said group being carbocyclic or heterocyclic, or (2) a thiocarbonyl group.

23. The process of claim 22 wherein Compound I has a formula selected from the group consisting of:

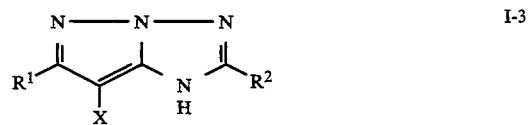

I-3

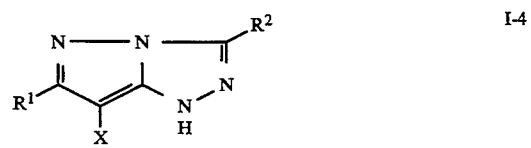

I-4

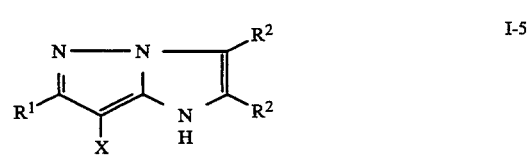

I-5

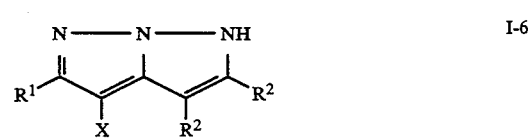

I-6

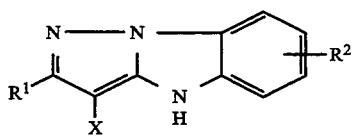  I-7

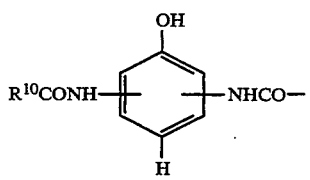  I-12

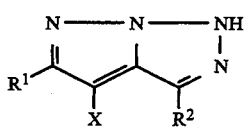  I-8

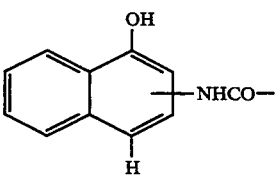  I-13

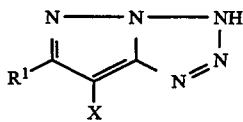  I-9

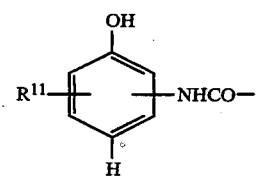  I-14

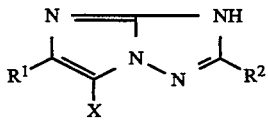  I-10

24. The process of claim 23 wherein Compound I has the formula of Compound I-3.

25. The process of claim 23 wherein Compound I has the structure I-1 and both $Z_a$ and $Z_b$ are nitrogen.

26. The process of claim 23 wherein Compound I has the structure I-2 and both $Z_a$ and $Z_c$ are nitrogen.

27. The process of claim 1 wherein Compound I has the formula I-11:

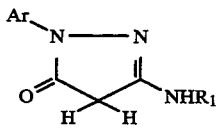  I-11 wherein:
Ar is an unsubstituted aryl group or an aryl group substituted with one or more substituents selected from halogen atoms and cyano, alkylsulfonyl, arylsulfonyl, sulfamoyl, sulfonamido, carbamoyl, carbonamido, alkoxy, acyloxy, aryloxy, alkoxycarbonyl, aryloxycarbonyl, ureido, nitro, alkyl, and trifluoromethyl, or Ar is an aryl group substituted with a group which forms a link to a polymeric chain;

$R_1$ is a substituted or unsubstituted acyl or phenyl group, the substituents of $R_1$ being individually selected from halogen atoms, and alkyl, aryl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyl, acyloxy, ureido, imido, carbamate, heterocyclic, cyano, trifluoromethyl, alkylthio, nitro, carboxyl and hydroxyl groups, provided that $R_1$ contains at least 6 carbon atoms or the $R_1$ substituents may individually comprise a group which forms a link to a polymeric chain.

28. The process of claim 1 wherein Compound I has the formula I-12, I-13, or I-14:

wherein $R^{10}$ represents a ballast group or a substituted or unsubstituted alkyl or aryl group; and
$R^{11}$ represents one or more halogen atoms, alkyl having 1 to 4 carbon atoms or alkoxy having 1 to 4 carbon atoms.

29. The process of claim 1 wherein Compound I has the formula I-15 or I-16:

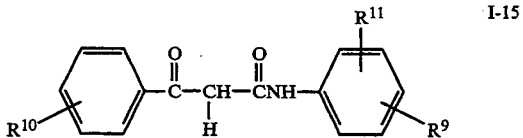  I-15

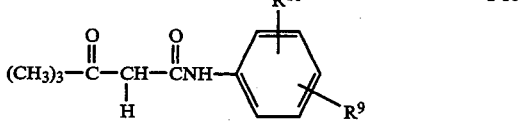  I-16 where $R^{10}$ represents a ballast group or a substituted or unsubstituted alkyl or aryl group,
$R^9$ is selected from the group consisting of hydrogen, a ballast group, or unsubstituted or substituted alkoxy, alkoxycarbonyl, alkanesulfonyl, arenesulfonyl, aryloxycarbonyl, carbonamido, carbamoyl, sulfonamido, or sulfamoyl,
$R^{11}$ is hydrogen or one or more halogen, lower alkyl, lower alkoxy, or a ballast group.

30. The process of claim 29 wherein Compound I has the formula (I-16).

31. The process of claim 1 wherein Compound II is a thiocarbonyl compound and the process includes the additional subsequent steps of hydrolyzing the thioether produced by the reaction between Compounds I and II and then displacing the hydrogen of the hydrolyzed compound with a substituted or unsubstituted alkyl group.

32. The process of claim 31 wherein the displacement is accomplished via Sn2 nucleophilic displacement or conjugate addition.

33. The process of claim 31 wherein the nucleophilic displacement is accomplished through reaction with an alkyl halide or sulfonyloxy compound.

34. The process of claim 1 wherein A and R contain up to 42 carbon atoms.

* * * * *